United States Patent
Mochitate et al.

[11] Patent Number: 5,832,056
[45] Date of Patent: Nov. 3, 1998

[54] X-RAY EXAMINATION APPARATUS

[75] Inventors: Mikio Mochitate, Matsudo; Hiroshi Abe; Hideki Kohno, both of Kashiwa, all of Japan

[73] Assignee: Hitachi, Medical Corporation, Tokyo, Japan

[21] Appl. No.: 716,545

[22] Filed: Sep. 19, 1996

[30] Foreign Application Priority Data

Sep. 22, 1995 [JP] Japan .................................. 7-244409

[51] Int. Cl.⁶ .................................................. H05G 1/06
[52] U.S. Cl. ........................ 378/195; 378/196; 378/208
[58] Field of Search .................................. 378/193–198, 378/209, 208

[56] References Cited

U.S. PATENT DOCUMENTS 5,327,474  7/1994  Inoue et al. ............................... 378/20
5,661,772  8/1997  Bar et al. ................................. 378/195

FOREIGN PATENT DOCUMENTS

6-54843  1/1994  Japan .

Primary Examiner—Don Wong
Attorney, Agent, or Firm—Antonelli, Terry, Stout & Kraus, LLP

[57] ABSTRACT

An X-ray examination apparatus includes an X-ray diagnosis apparatus (first imaging area), an X-ray CT apparatus (second imaging area), a bed, and the X-ray diagnosis apparatus and the X-ray CT apparatus are arranged along a path of movement of a top plate of the bed in such a manner that the first and second imaging areas are spaced a predetermined distance from each other in a path of movement of the top plate. There is provided a top plate reciprocal movement control means which through operations of switches moves the top plate forward and backward between a first top plate position where a desired part of the patient is positioned at the first imaging area and a second top plate position where the top plate is spaced from the first top plate position toward the X-ray CT apparatus by a distance corresponding to the distance between the first and second imaging areas so that in the reciprocal movement of the two apparatuses, the top plate can be stopped at the first and second top plate position.

17 Claims, 3 Drawing Sheets

X-RAY EXAMINATION APPARATUS

BACKGROUND OF THE INVENTION

1. Field of the Invention

This invention relates to an X-ray examination apparatus in which an IVR (Interventional Radiology) operation can be suitably performed while using an X-ray diagnosis apparatus (particularly for examining circulatory organs), having an X-ray tube and an image intensifier disposed in opposed relation to each other, an X-ray CT (computed tomography) apparatus.

2. Related Art

There is known an X-ray examination apparatus (see Japanese Patent Unexamined Publication No. 6-54843) which comprises an X-ray diagnosis apparatus having an X-ray tube and an image intensifier which face each other through a first imaging area, an X-ray CT apparatus for producing sectional images of the object to be examined (hereinafter referred to as "patient") who is positioned in a second imaging area, and a bed which comprises a top plate for the laying-down of the patient thereon, and a top plate support unit supporting the top plate in a manner to allow the movement of the top plate in a direction of the length thereof, and the X-ray diagnosis apparatus and the X-ray CT apparatus are arranged along a path of movement of the top plate in such a manner that the first and second imaging areas are spaced a predetermined distance from each other in the path of movement of the top plate.

In such an X-ray examination apparatus, merely by moving the top plate of the bed, the patient can be transported between the two imaging areas of the X-ray diagnosis apparatus and the X-ray CT apparatus, and therefore a surgical operation can be conducted easily and properly by suitably and selectively referring to a fluoroscopic image, produced by the X-ray diagnosis apparatus, and a sectional image produced by the X-ray CT apparatus.

Such an X-ray examination apparatus is useful particularly when for example, an angiographic diagnosis (in which case a catheter is used) or an embolic operation is conducted while using the circulatory organ-examining X-ray diagnosis apparatus, and then the three-dimensional position of the catheter or the embolic part is grasped by a sectional image produced by the X-ray CT apparatus.

In the above conventional X-ray examination apparatus, any consideration has not been given to the positioning of the top plate (and hence the patient) at the X-ray diagnosis apparatus and the X-ray CT apparatus, and the operator has manually operated the top plate support unit of the bed to move the top plate, thereby positioning the top plate at each of the two apparatuses. Therefore, much time and labor have been required for the positioning operation, and besides the positioning precision varies from one operator to another, and it has been desired to improve these problems.

SUMMARY OF THE INVENTION

It is a first object of this invention to provide an X-ray examination apparatus in which when the imaging by an X-ray CT apparatus is to be effected after the imaging by an X-ray diagnosis apparatus is effected, or when the imaging by the X-ray diagnosis apparatus is to be effected after the imaging by the X-ray CT apparatus is effected, a top plate of a bed (and hence the patient) can be positioned rapidly, easily and accurately at the imaging area of the X-ray CT apparatus or the imaging area of the X-ray diagnosis apparatus.

A second object of the invention is to provide an X-ray examination apparatus in which when the spiral scan imaging by an X-ray CT apparatus is to be effected after the imaging by an X-ray diagnosis apparatus is effected, or when the imaging by the X-ray diagnosis apparatus is to be effected after the spiral scan-imaging by the X-ray CT apparatus is effected, a top plate of a bed (and hence the patient) can be positioned rapidly, easily and accurately at the spiral scan imaging-preparing position of the X-ray CT apparatus or the imaging area of the X-ray diagnosis apparatus.

The first object of the invention has been achieved by an X-ray examination apparatus comprising an X-ray diagnosis apparatus including an X-ray tube and an image intensifier which face each other through a first imaging area;

an X-ray CT apparatus for producing a sectional image of the object positioned in a second imaging area;

a bed which comprises a top plate for the laying-down of the object (hereinafter referred to as "patient") thereon, and a top plate support unit supporting the top plate in a manner to allow the movement of the top plate in a direction of a length thereof, the X-ray diagnosis apparatus and the X-ray CT apparatus being arranged along a path of movement of the top plate in such a manner that the first and second imaging areas are spaced a predetermined distance from each other in the path of movement of the top plate; and top plate reciprocal movement control means which through operations of switches, moves the top plate forward and backward between a first top plate position where a desired part of the patient, laid down on the top plate, is positioned at the first imaging area and a second top plate position where the top plate is spaced from the first top plate position toward the X-ray CT apparatus by a distance corresponding to the distance between the first and second imaging areas so that in the reciprocal movement of the top plate between the X-ray diagnosis apparatus and the X-ray CT apparatus, the top plate can be stopped at the first and second top plate positions.

In this X-ray examination apparatus, through operations of the switches, the top plate reciprocal movement control means moves the top plate forward and backward between the first top plate position where the desired part of the patient, laid down on the top plate, is positioned at the first imaging area and the second top plate position (top plate position for CT scan imaging) where the top plate is spaced from the first top plate position toward the X-ray CT apparatus by a distance corresponding to the distance (constant value) between the first and second imaging areas so that in the reciprocal movement of the top plate between the X-ray diagnosis apparatus and the X-ray CT apparatus, the top plate can be stopped at the first and second top plate positions. With this construction, when the imaging by the X-ray CT apparatus is to be effected after the imaging by the X-ray diagnosis apparatus is effected, or when the imaging by the X-ray diagnosis apparatus is to be effected after the imaging by the X-ray CT apparatus is effected, the top plate (and hence the patient) can be positioned rapidly, easily and accurately at the imaging area of the X-ray CT apparatus or the imaging area of the X-ray diagnosis apparatus.

The second object of the invention has been achieved by an X-ray examination apparatus comprising an X-ray diagnosis apparatus including an X-ray tube and an image intensifier which face each other through a first imaging area;

an X-ray CT apparatus for producing a sectional image of the patient positioned in a second imaging area;

a bed which comprises a top plate for the laying-down of the patient thereon, and a top plate support unit supporting the top plate in a manner to allow the movement of the top plate in a direction of a length thereof, the X-ray diagnosis apparatus and the X-ray CT apparatus being arranged along a path of movement of the top plate in such a manner that the first and second imaging areas are spaced a predetermined distance from each other in the path of movement of the top plate, and the X-ray CT apparatus being capable of spiral scanning; and top plate reciprocal movement control means which before or after the spiral scanning, through operations of switches, moves the top plate forward and backward between a first top plate position where a desired part of the patient, laid down on the top plate, is positioned at a first imaging area and a second top plate position where the top plate is spaced from the first top plate position toward the X-ray CT apparatus by a distance obtained by subtracting at least a half of a dimension of a visual field of the image intensifier in the direction of movement of the top plate from the distance between the first and second imaging areas so that in the reciprocal movement of the top plate between the X-ray diagnosis apparatus and the X-ray CT apparatus, the top plate can be stopped at the first and second top plate positions.

In this X-ray examination apparatus, before or after the spiral scanning, through operations of the switches, the top plate reciprocal movement control means moves the top plate forward and backward between the first top plate position where a desired part of the patient, laid down on the top plate, is positioned at the first imaging area and the second top plate position (top plate position for preparation for CT spiral scan imaging) where the top plate is spaced from the first top plate position toward the X-ray CT apparatus by a distance obtained by subtracting at least a half of a dimension of the visual field of the image intensifier in the direction of movement of the top plate from the distance (constant value) between the first and second imaging areas so that in the reciprocal movement of the top plate between the X-ray diagnosis apparatus and the X-ray CT apparatus, the top plate can be stopped at the first and second top plate positions. With this construction, when the spiral scan imaging by the X-ray CT apparatus is to be effected after the imaging by the X-ray diagnosis apparatus is effected, or when the imaging by the X-ray diagnosis apparatus is to be effected after the spiral scan-imaging by the X-ray CT apparatus is effected, the top plate (and hence the patient) can be positioned rapidly, easily and accurately at the spiral scan imaging-preparing position of the X-ray CT apparatus or the imaging area of the X-ray diagnosis apparatus.

DESCRIPTION OF THE PREFERRED EMBODIMENTS

A preferred embodiment of the present invention will now be described with reference to the drawings.

Figure 1:
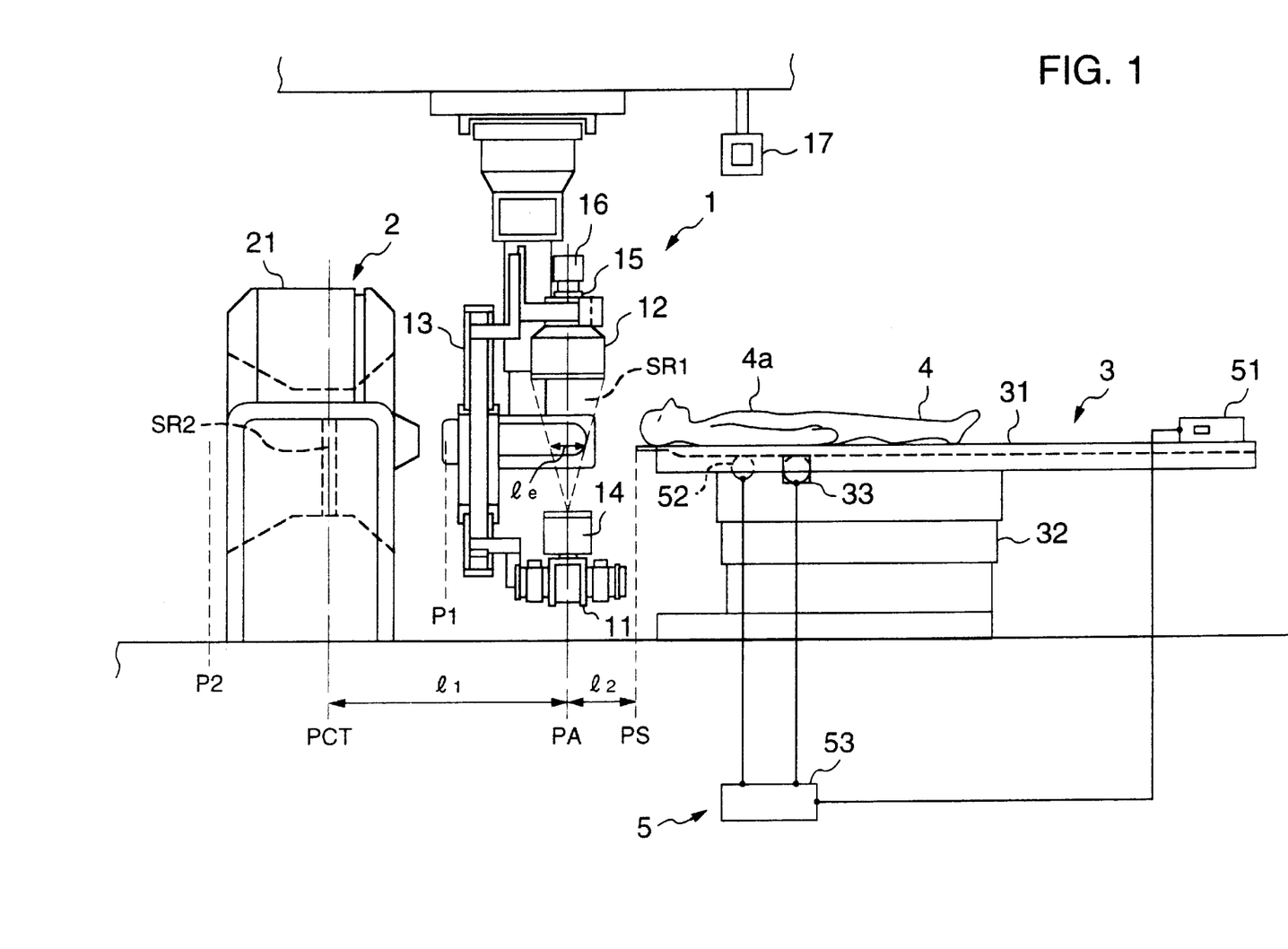
FIG. 1 is a side-elevational view of one preferred embodiment of an X-ray examination apparatus of the present invention.

FIG. 1 is a side-elevational view of one preferred embodiment of an X-ray examination apparatus of the invention. In FIGS. 1, an X-ray diagnosis apparatus 1 comprises an X-ray tube 11 for emitting X-rays, and an image intensifier 12 for converting the X-rays into visible light, the X-ray tube 11 and the image intensifier 12 facing each other through a first imaging area SR1. Here, the X-ray diagnosis apparatus is one for examining circulatory organs. The X-ray tube 11 and the image intensifier 12 are mounted on opposite ends of a C-shaped arm 13, respectively, and by driving the C-shaped arm 13 in various manners, the patient in the first imaging area SR1 can be photographed in various directions. A diaphragm 14 is mounted on an X-ray emitting side of the X-ray tube 11, and a television camera 16 is mounted on an output side of the image intensifier 12 through an optical system 15. An output signal of this television camera 16 is fed to a image processing device (not shown), and for example, an image of a vessel is obtained from a plurality of fluoroscopic images, and this vessel image is displayed on a monitor 17 for observation and diagnosis purposes.

An X-ray CT (computed tomography) apparatus 2 for producing sectional images of the patient positioned in a second imaging area SR2 comprises a gantry 21. The gantry 21 has an X-ray source and an X-ray detector (both of which are not shown) facing each other through the second imaging area SR2. Here, the X-ray CT apparatus 2 is of the R—R type (the third generation).

A bed 3 comprises a top plate 31 on which the patient 4 is adapted to be laid down, and a top plate support unit 32 supporting the top plate 31 in a manner to allow the movement of the top plate 31 in a direction of the length thereof (that is, right and left directions in the drawings). The top plate support unit 32 also moves the top plate 31 upward and downward. A motor 33 is a drive source for moving the top plate 31 in the direction of the length thereof.

The X-ray diagnosis apparatus 1 and the X-ray CT apparatus 2 are arranged along a path of movement of the top plate 31 in such a manner that the first and second imaging areas SR1 and SR2 are spaced a predetermined distance from each other in the path of movement of the top plate 31. In other words, the bed 3 is for common use for the X-ray diagnosis apparatus 1 and the X-ray CT apparatus.

Through operations of switches, top plate reciprocal movement control means 5 moves the top plate 31 forward and backward (that is, reciprocally) between a first top plate position P1 where a desired part of the patient 4, laid down on the top plate 31, is positioned at the first imaging area SR1 and a second top plate position (top plate position for CT scan imaging) P2 where the top plate 31 is spaced from the first top plate position P1 toward the X-ray CT apparatus 2 by a distance corresponding to the distance (constant value) l1 between the first and second imaging areas SR1 and SR2 so that in the reciprocal movement of the top plate 31 between the X-ray diagnosis apparatus 1 and the X-ray CT apparatus 2, the top plate 31 can be stopped at the first and second top plate positions P1 and P2.

Figure 2:
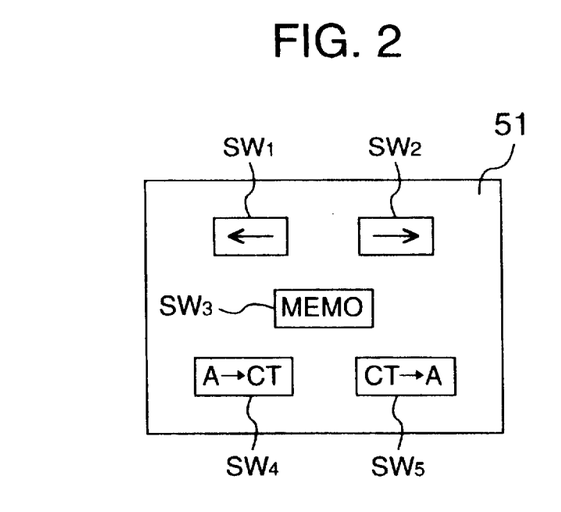
FIG. 2 is a plan view of an operating device of the apparatus of FIG. 1.

This top plate reciprocal movement control means 5 comprises an operating device 51 for operating the switches, a top plate movement amount detector 52 for detecting the amount PX of forward movement (left movement in the drawings) of the top plate 31 from a stand-by position (rearmost position) PS, and a controller 53 for moving the top plate 31 forward and backward in accordance with the operation of the operating device 31. The top plate 31 can also make ordinary movements in addition to the above reciprocal movement (that is, forward and backward movements). Therefore, as shown in FIG. 2, the operating device 51 includes a forward movement switch button SW1 for making an ordinary forward movement (in the left-hand direction in the drawings) of the top plate 31, a backward movement switch button SW2 for making an ordinary backward movement (in the right-hand direction in the drawings) of the top plate 31, a first top plate position storage (memory) switch button SW3 for storing the position of the top plate 31 where the desired part of the patient 4, laid down on the top plate 31, is positioned at the first imaging area SR1, that is, the first top plate position P1, in a memory (not shown) in the controller 53, an A→CT switch button SW4 for moving (or advancing) the top plate 31 forward from the first top plate position P1 to the second top plate position P2, and a CT→A switch button SW5 for moving (or returning) the top plate 31 in the opposition direction, that is, backward from the second top plate position P2 to the first top plate position P1.

Only during the time when the forward (left) movement switch button SW1 or the backward (right) movement switch button SW2 is depressed, the top plate 31 can be continuously moved forward or backward within a predetermined range between the stand-by position (rearmost position) PS and a predetermined foremost position. When the A→CT switch button SW4 is depressed once (that is, by a one-touch operation), the top plate 31 is moved forward (or advances) from the first top plate position P1 to the second top plate position P2. Similarly, when the CT→A switch button SW5 is depressed once (that is, by a one-touch operation), the top plate 31 is moved backward (that is, returned) from the second top plate position P2 to the first top plate position P1.

The top plate movement amount detector 52 includes an absolute-type rotary encoder for converting the movement of the top plate 31 in the direction of the length thereof into a rotary motion so as to detect the amount of this movement.

As can be seen from FIG. 1, the distance l1 between the first and second imaging areas SR1 and SR2 is the distance between the center position PA of the first imaging area SR1 and the center position PCT of the second imaging area SR2. Thus, here, the positions of the first and second imaging areas SR1 and SR2 mean their center positions PA and PCT, respectively. The position of the top plate 31 means the position of its front end (left end). Reference character l2 denotes the distance between the stand-by position PS of the top plate 31 and the first imaging area SR1 (the position PA). Reference numeral 4a denotes the desired part (here, the chest) of the patient 4 to be examined.

The operation of the above X-ray examination apparatus will now be described with reference to FIGS. 1 to 4.

Figure 3:
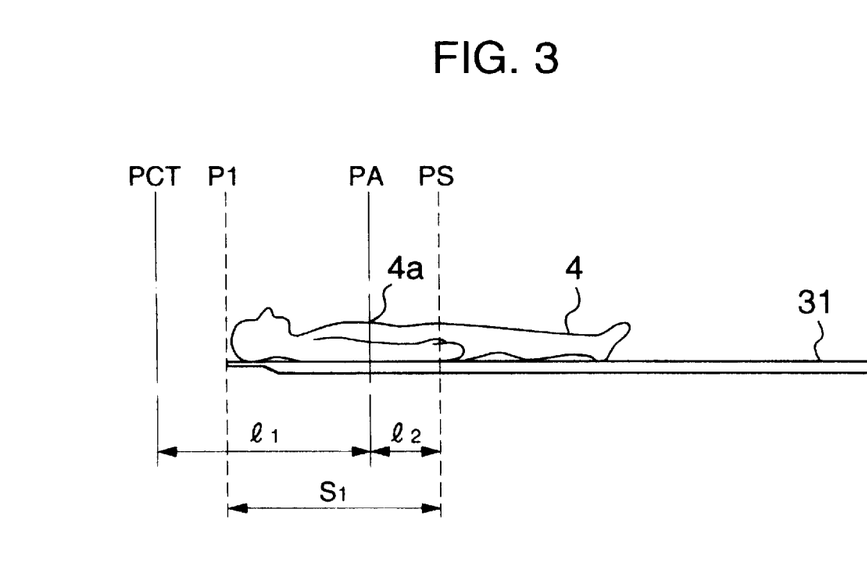
FIG. 3 is a view explanatory of the operation of the X-ray examination apparatus of FIG. 1, showing a top plate located in an examination position where the examination is conducted by a circulatory organ-examining X-ray diagnosis apparatus.

Now, the desired part (here, the chest 4a) of the patient 4 is positioned at the first imaging area SR1 (the position PA) for an angiographic examination by the circulatory organ-examining X-ray diagnosis apparatus 1. In this condition, the top plate 31, on which the patient 4 is laid down, is stopped at the first top plate position P1 spaced forwardly a distance S1 from the stand-by position PS, as shown in FIG. 3.

For moving the top plate 31 from the stand-by position PS to the first top plate position P1, the operator continues to depress the forward movement switch button SW1 of the operating device 51 until the chest 4a reaches the first imaging area SR1 (the position PA), and during this time period, the motor 33 is driven through the controller 53 to move the top plate 31. At this time, the distance S1 is detected by the top plate movement amount detector 52, and can be stored in the above-mentioned memory in the controller 53. The distance l1 between the first and second imaging areas SR1 and SR2 is set to a predetermined distance when the circulatory organ-examining X-ray diagnosis apparatus 1 and the X-ray CT apparatus are installed, or before the examination by the two apparatuses 1 and 2 is started if the two apparatuses 1 and 2 are movable in the left and right directions, and this distance l is also stored in the above memory in the controller 53.

The depression of the forward movement switch button SW1 is stopped when the chest 4a reaches the first imaging area SR1 (the position PA), and then by depressing the first top plate position storage switch button SW3, the first top plate position P1 is stored in the above memory in the controller 53.

In this condition, the circulatory organ-examining X-ray diagnosis apparatus 1 is operated to obtain, for example, an image of the vessel in the chest 4a, and this image is displayed on the monitor 17, and an IVR operation and so on are performed while conducting the examination such as observation and a diagnosis.

Figure 4:
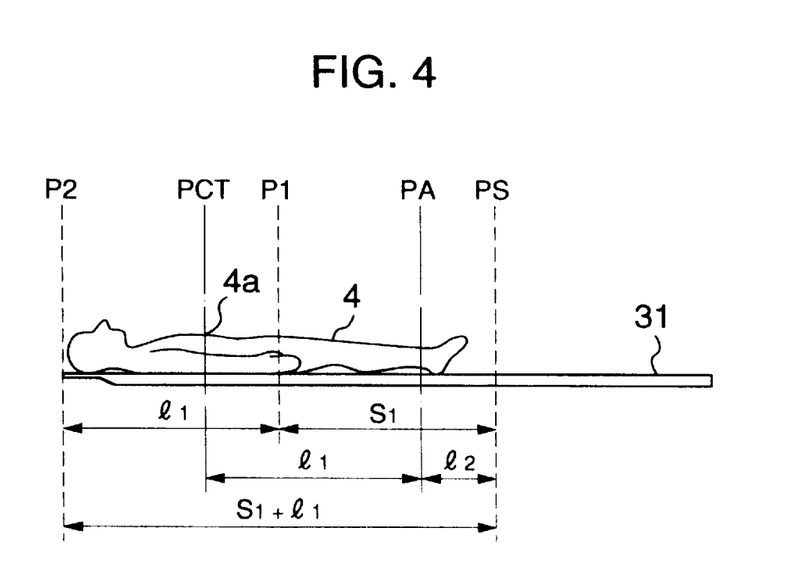
FIG. 4 is a view similar to FIG. 3, but showing the top plate located in an examination position where the examination is conducted by an X-ray CT apparatus.

If it is desired to grasp the three-dimensional position of a catheter or an embolus through a sectional image to be produced by the X-ray CT apparatus 2 after the necessary operation is performed, the operator depresses the A→CT switch button SW4 of the operating device 51 once. As a result, the controller 53, while referring to the output value of the top plate movement amount detector 52, causes the motor 33 to be driven, thereby moving the top plate 31 forward. When the output value of the top plate movement amount detector 52 coincides with the distance l1 between the first and second imaging areas SR1 and SR2, the controller 53 causes the motor 33 to stop, so that the top plate 31 is stopped at the second top plate position P2, thus completing the forward (or advancing) movement of the top plate 31.

In this condition, the chest 4a of the patient 4 is positioned at the second imaging area SR2 (the position PCT) as shown in FIG. 4, and a sectional image of the chest 4a can be produced by operating the X-ray CT apparatus 2. The sectional image thus obtained is displayed on the monitor 17 instead of the vessel image. If the monitor 17 is of the multi-image display type, the sectional image of the chest 4a is displayed on that portion of the monitor 17 adjacent to the vessel image on this monitor 17 so that the three-dimensional position of the catheter or the embolus can be grasped.

Thereafter, when an image of a vessel in the chest 4a of the patient 4 or other is to be again obtained, and is to be displayed on the monitor 17 so that the observation, a diagnosis, or an IVR operation or other operation can be performed, the operator depresses the CT→A switch button SW5 once. As a result, the controller 53, while subtracting the output value of the top plate movement amount detector 53 from the above distance l1, causes the motor 33 to be driven, thereby moving the top plate 31 backward. When the value of the above subtraction becomes zero, the controller 53 causes the motor 33 to stop, so that the top plate 31 is stopped at the first top plate position P1, thus completing the backward (returning) movement of the top plate 31.

In this condition, the chest 4a of the patient 4 is positioned at the first imaging area SR1 (the position PA) as shown in FIG. 3, and the image of the vessel in the chest 4a can be obtained by operating the circulatory organ-examining X-ray diagnosis apparatus 1. The vessel image thus obtained is displayed on the monitor 17 instead of the image already displayed on this monitor 17, and is used for observation, diagnosis and so on, and if necessary, an IVR operation or other is again performed.

Then, the above operation is repeated a required number of times. The movement of the top plate 31 from the first top plate position P1 to the second top plate position P2, that is, the forward (advancing) movement of the patient chest 4a from the first imaging area SR1 to the second imaging area SR1, can be effected by operating the A→CT switch button SW4 with one touch. Also, the movement of the top plate 31 from the second top plate position P2 to the first top plate position P1, that is, the backward (returning) movement of the patient chest 4a from the second imaging area SR2 (the position PCT) to the first imaging area SR1 (the position PA), can be effected by operating the CT→A switch button SW5 with one touch.

Another (second) embodiment of the present invention will now be described. In FIG. 1, an X-ray examination apparatus of this embodiment is similar to the X-ray examination apparatus of the first embodiment except that an X-ray CT apparatus 2 is capable of spiral scanning and that a top plate reciprocal movement control means 5 is constructed as follows. More specifically, before or after the spiral scanning, through the operation of switches, the top plate reciprocal movement control means 5 moves a top plate 31 forward and backward (that is, reciprocally) between a first top plate position P1 where a desired part of the patient 4, laid down on the top plate 31, is positioned at a first imaging area SR1, and a second top plate position (top plate position for preparation for CT spiral scan imaging) P2 where the top plate 31 is spaced from the first top plate position P1 toward the X-ray CT apparatus 2 by a distance obtained by subtracting at least a half of a dimension le of a visual field of an image intensifier 12 in the direction of movement of the top plate 31 from the distance (constant value) l1 between the first and second imaging areas SR1 and SR2 so that in the reciprocal movement of the top plate 31 between the X-ray diagnosis apparatus 1 and the X-ray CT apparatus 2, the top plate 31 can be stopped at the first and second top plate positions P1 and P2.

Figure 5:
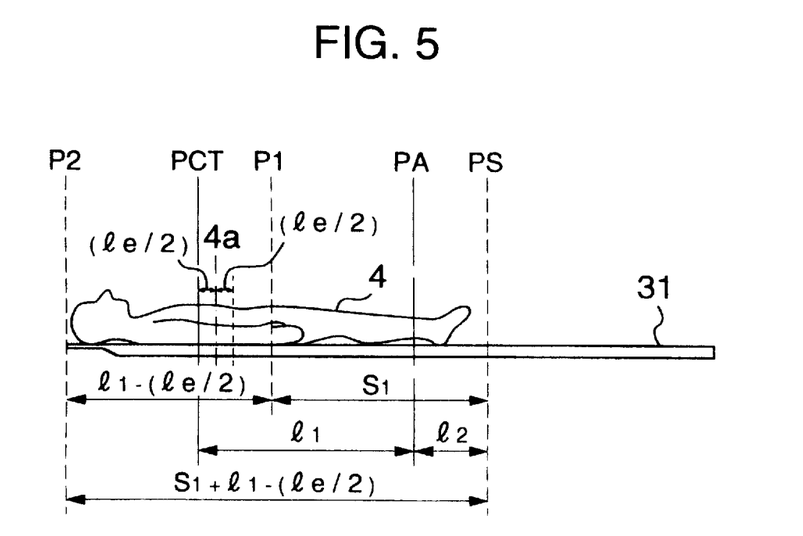
FIG. 5 is a view showing a top plate located in a position for preparation for a spiral scan examination by an X-ray CT apparatus in a modified X-ray examination apparatus.

In the second embodiment, in order that a three-dimensional CT data, corresponding at least to the dimension le of the visual field of the image intensifier 12 in the direction of movement of the top plate 13, can be measured by the X-ray CT apparatus 2 capable of spiral scanning, the second top plate position P2 is the top plate position for preparation for CT spiral scan imaging, and is not the top plate position for CT scan imaging as in the first embodiment. This top plate position for preparation for CT spiral scan imaging is the top plate position where the desired part (here, the chest 4a) of the patient 4, laid down on the top plate 31, is shifted from the second imaging area SR2 (the position PCT) toward the first top plate position P1 by an arbitrary value ln not less than a half of the dimension le, and in other words, this top plate position is the top plate position shifted forward from the stand-by position (rearmost position) PS of the top plate 31 by {S1+(l1−ln)} (ln≧le/2). FIG. 5 is an illustration showing this positional relation, and here, ln=le/2 is established.

Now, let's assume that the top plate 31 is located at the angiographic examination position as shown in FIG. 3. In this condition, when the operator operates an A→CT switch button SW4 of an operating device 51 with one touch, a controller 53, while referring to an output value of a top plate movement amount detector 52, causes a motor 33 to be driven, thereby moving the top plate 31 forward. When the output value of the top plate movement amount detector 52 coincides with the above (l1−ln), the controller 53 causes the motor 33 to stop, so that the top plate 31 is stopped at the second top plate position (the top plate position for preparation for CT spiral scan imaging) P2, thus completing the forward (advancing) movement of the stop plate 31.

Then, by operating the X-ray CT apparatus 2 while moving the top plate 31 forward, the spiral scan imaging is carried out. Thereafter, when an image of a vessel in the chest 4a of the patient 4 or other is to be again obtained, and is to be displayed on the monitor 17 so that the observation, a diagnosis, or an IVR operation or other operation can be performed, the operator operates the CT→A switch button SW5 with one touch. As a result, the controller 53 adds a forward movement amount lm (lm≧le) during the spiral scanning to the above (l1−ln), and the controller 53, while subtracting the output value of the top plate movement amount detector 52 from this addition value, (l1−ln)+lm, causes the motor 33 to be driven, thereby moving the top plate 31 backward. When the value of the above subtraction becomes zero, the controller 53 causes the motor 33 to stop, so that the top plate 31 is stopped at the first top plate position P1, thus completing the backward (returning) movement of the top plate 31.

Then, the above operation is repeated a required number of times. At this time, as in the first embodiment, the forward (advancing) movement of the top plate 31 from the first top plate position P1 to the second top plate position (top plate position for preparation for CT spiral scan imaging) P2 can be effected by operating the A→CT switch button SW4 with one touch, and the backward (returning) movement of the top plate 31 from the second top plate position (top plate position for preparation for CT spiral scan imaging) P2 to the first top plate position P1 can be effected by operating the CT→A switch button SW5 with one touch. The above ln of a predetermined value may be prestored in the controller 53, or any desired value of the l can be stored in the controller 53.

Only during the time when the A→CT switch button SW4 and the CT→A switch button SW5 are depressed, the top plate 31 can be continuously moved as described above for the forward movement switch button SW1 and the backward movement switch button SW2. With such a construction, if it is desired to stop the top plate 31 for some emergency reason during the forward movement and the backward movement, this can be done merely by stopping the depression of the switch button, and this provides the enhanced safety. Anyway, regardless of whether or not the switch button SW4 or the switch button SW5 is in its depressed condition, the movement of the top plate 31 through the operation of the A→CT switch button SW4 or the CT→A switch button SW5 is stopped when the top plate 31 reaches the second top plate position P2 or the first top plate position P1.

A film imaging system may be added to the X-ray diagnosis apparatus 1 so that X-ray film imaging for producing fluoroscopic images can be effected.

In the X-ray examination apparatus of the first embodiment, through operations of the switches, the top plate can be moved forward and backward between the first top plate position where the desired part of the patient is positioned at the first imaging area and the second top plate position (top plate position for CT scan imaging) where the top plate is spaced from the first top plate position toward the X-ray CT apparatus by a distance corresponding to the distance between the first and second imaging areas so that in the reciprocal movement of the top plate between the X-ray diagnosis apparatus and the X-ray CT apparatus, the top plate can be stopped at the first and second top plate positions. With this construction, when the imaging by the X-ray CT apparatus is to be effected after the imaging by the X-ray diagnosis apparatus is effected, or when the imaging by the X-ray diagnosis apparatus is to be effected after the imaging by the X-ray CT apparatus is effected, the top plate (and hence the patient) can be positioned rapidly, easily and accurately at the imaging area of the X-ray CT apparatus or the imaging area of the X-ray diagnosis apparatus.

In the X-ray examination apparatus of the second embodiment, before or after the spiral scanning, through operations of the switches, the top plate can be moved forward and backward between the first top plate position where a desired part of the patient is positioned at the first imaging area and the second top plate position (top plate position for preparation for CT spiral scan imaging) where the top plate is spaced from the first top plate position toward the X-ray CT apparatus by a distance obtained by subtracting at least a half of a dimension of the visual field of the image intensifier in the direction of movement of the top plate from the distance between the first and second imaging areas so that in the reciprocal movement of the top plate between the X-ray diagnosis apparatus and the X-ray CT apparatus, the top plate can be stopped at the first and second top plate positions. With this construction, when the spiral scan imaging by the X-ray CT apparatus is to be effected after the imaging by the X-ray diagnosis apparatus is effected, or when the imaging by the X-ray diagnosis apparatus is to be effected after the spiral scan-imaging by the X-ray CT apparatus is effected, the top plate (and hence the patient) can be positioned rapidly, easily and accurately at the spiral scan imaging-preparing position of the X-ray CT apparatus or the imaging area of the X-ray diagnosis apparatus.

What is claimed is:

1. An X-ray examination apparatus comprising:
    an X-ray diagnosis apparatus including an X-ray tube and an image intensifier apparatus which face each other through a first imaging area in which a patient is positioned;
    a spirally scanning X-ray CT apparatus for producing a sectional image of the patient positioned in a second imaging area; and
    a bed provided with a table on which the patient is laid down and a table-supporting unit for supporting said table movably in a longitudinal direction of said table;
    said X-ray diagnosis apparatus and said spirally scanning X-ray CT apparatus being located along a path of movement of said table so that said first and second imaging areas are located at positions spaced apart from each other by a predetermined distance;
    said X-ray examination apparatus further comprising:
        a memory for storing a distance obtained by subtracting at least a half of a dimension of a visual field of said image intensifier in the direction of movement of said table from said predetermined distance between said first and second imaging areas;
        a detector for detecting an amount of movement of said table; and
        table control means for comparing said movement amount of said table with a distance obtained by adding a forward movement amount occurring on spiral scanning of the patient to said distance obtained by subtracting at least a half of a dimension of a visual field of said image intensifier in the direction of movement of said table from said predetermined distance between said first and second imaging areas, to thereby automatically move said table to said imaging center of said first imaging area from a table position obtained by moving said table from said imaging center of said first imaging area toward said spirally scanning X-ray CT apparatus by a distance obtained by adding a forward movement amount occurring on spiral scanning of the patient to said distance obtained by subtracting at least a half of a dimension of a visual field of said image intensifier in the direction of movement of said table from said predetermined distance between said first and second imaging areas, and to automatically perform the stopping of said table.

2. An X-ray examination apparatus comprising:
    an X-ray diagnosis apparatus including an X-ray tube and an image intensifier apparatus which face each other through a first imaging area in which a patient is positioned;
    a spirally scanning X-ray CT apparatus for producing a sectional image of the patient positioned in a second imaging area; and
    a bed provided with a table on which the patient is laid down and a table-supporting unit for supporting said table movably in a longitudinal direction of said table;
    said X-ray diagnosis apparatus and said spirally scanning X-ray CT apparatus being located along a path of movement of said table so that said first and second imaging areas are located at positions spaced apart from each other by a predetermined distance;
    said X-ray examination apparatus further comprising:
        a memory for storing a distance obtained by subtracting at least a half of a dimension of a visual field of said image intensifier in the direction of movement of said table from said predetermined distance between said first and second imaging areas;
        a detector for detecting an amount of movement of said table; and
        table control means for comparing said movement amount of said table with said distance obtained by subtracting at least a half of a dimension of a visual field of said image intensifier in the direction of movement of said table from said predetermined distance between said first and second imaging areas, to automatically move the table from the imaging center of the first imaging area toward the spirally scanning X-ray CT apparatus by said distance obtained by subtracting at least a half of a dimension of a visual field of the image intensifier in the direction of movement of said table from said predetermined distance between said first and second imaging areas, or vice versa and to automatically perform the stopping of said table.

3. An X-ray examination apparatus comprising:
    an X-ray diagnosis apparatus including an X-ray tube and an X-ray image receptor for converting an X-ray which is emitted from the X-ray tube and which is transmitted through a patient to be examined, into image information, said X-ray diagnosis apparatus being provided with a first imaging area between the X-ray tube and the X-ray image receptor;

an X-ray CT apparatus for producing a sectional image of the patient, said X-ray CT apparatus being provided with a second imaging area for obtaining said sectional image, a center of said second imaging area being spaced apart from a center of said first imaging area by a distance;

a bed which comprises a table on which the patient is laid down and which is movable between said first imaging area and said second imaging area; and table movement control means which, through one-touch switch operation, moves said table in a direction from said first imaging area to said second imaging area and vice versa by said distance defined between said centers of said first and second imaging area when imaging is performed after switching between said X-ray diagnosis apparatus and X-ray CT apparatus.

4. An X-ray examination apparatus according to claim 3, wherein said table movement control means comprises a memory circuit for memorizing said distance between said first and second imaging areas, a detection mechanism for detecting the amount of movement of said table, and means for deciding a stop position of said table from both said distance between said first and second imaging areas and said amount of table movement.

5. An X-ray examination apparatus according to claim 4, wherein said distance between said first and second imaging areas is set when said X-ray diagnosis apparatus and X-ray CT apparatus are installed, said set distance being stored in said memory circuit.

6. An X-ray examination apparatus according to claim 4, wherein at least one of said X-ray diagnosis apparatus and said X-ray CT apparatus is movable in a direction of the movement of said table, said distance between said two imaging areas being stored by operating a switch connected to said memory circuit.

7. An X-ray examination apparatus according to claim 4, wherein said table movement control means further comprises a first one-touch switch for moving said table from said first imaging area of said X-ray diagnosis apparatus to said second imaging area of said X-ray CT apparatus, and a second one-touch switch for moving said table from said second imaging area of said X-ray CT apparatus to said first imaging area of said X-ray diagnosis apparatus.

8. An X-ray examination apparatus according to claim 7, wherein said table movement control means further comprises a switch which enables by continued pushing of said switch, to move said table to at least one of said first imaging area, second imaging area and any examining position of the patient.

9. An X-ray examination apparatus according to claim 3, wherein said table movement control means enables by the one-touch switch operation movement of said table having the patient laid down thereon and located at one of said first and second imaging areas into the other of said first and second imaging areas.

10. An X-ray examination apparatus comprising:

an X-ray diagnosis apparatus including an X-ray tube and an image intensifier apparatus which face each other through a first imaging area in which a patient is positioned;

an X-ray CT apparatus for producing a sectional image of the patient positioned in a second imaging area; and a bed provided with a table on which the patient is laid down and a table-supporting unit for supporting said table movably in a longitudinal direction of said table;

said X-ray diagnosis apparatus and X-ray CT apparatus being located along a path of movement of said table so that said first and second imaging areas are located at positions spaced apart from each other by a predetermined distance;

said X-ray examination apparatus further comprising table movement control means for moving or stopping said table to or at an imaging position of said first or second imaging areas while comparing the distance between said X-ray diagnosis apparatus and X-ray CT apparatus with the amount of the movement of said table.

11. An X-ray examination apparatus according to claim 10, wherein said table movement control means enables movement of said table until the amount of movement of said table becomes equal to the predetermined distance defined between said X-ray diagnosis apparatus and X-ray CT apparatus, and enables stopping of said table when said movement amount becomes equal to said predetermined distance.

12. An X-ray examination apparatus according to claim 10, wherein said table movement control means enables movement of said table until a difference between the amount of movement of said table and said predetermined distance defined between said X-ray diagnosis apparatus and X-ray CT apparatus becomes zero, and enables stopping of said table when said difference becomes zero.

13. An X-ray examination apparatus according to claim 10, wherein said table movement control means comprises a memory for stopping said predetermined distance defined between said X-ray diagnosis apparatus and X-ray CT apparatus, a detector for detecting an amount of movement of said table, and comparing means for comparing said predetermined distance between said X-ray diagnosis apparatus and X-ray CT apparatus with said movement amount of said table.

14. An X-ray examination apparatus comprising:

an X-ray diagnosis apparatus including an X-ray tube and an image intensifier apparatus which face each other through a first imaging area in which a patient is positioned;

a spirally scanning X-ray CT apparatus for producing a sectional image of the patient positioned in a second imaging area; and a bed provided with a table on which the patient is laid down and a table-supporting unit for supporting said table movably in a longitudinal direction of said table, said X-ray diagnosis apparatus and spirally scanning X-ray CT apparatus being located along a path of movement of said table so that said first and second imaging areas are located at positions spaced apart from each other by a predetermined distance;

said X-ray examination apparatus further comprising table movement control means for performing through one-touch switch operation the movement of said table between an imaging center of said first imaging area and a position where a spiral scanning of the patient is commenced in said second imaging area.

15. An X-ray examination apparatus comprising:

an X-ray diagnosis apparatus including an X-ray tube and an image intensifier apparatus which face each other through a first imaging area in which a patient is positioned;

a spirally scanning X-ray CT apparatus for producing a sectional image of the patient positioned in a second imaging area; and a bed provided with a table on which the patient is laid down and a table-supporting unit for supporting said table movably in a longitudinal direction of said table;

said X-ray diagnosis apparatus and said spirally scanning X-ray CT apparatus being located along a path of movement of said table so that said first and second imaging areas are located at positions spaced apart from each other by a predetermined distance;

said X-ray examination apparatus further comprising table movement control means for performing through one-touch switch operation the movement of said table between a position where a spiral scanning of the patient is finished in said second imaging area and an imaging center of said first imaging area.

16. An X-ray examination apparatus comprising:

an X-ray diagnosis apparatus including an X-ray tube and an image intensifier apparatus which face each other through a first imaging area in which a patient is positioned;

a spirally scanning X-ray CT apparatus for producing a sectional image of the patient positioned in a second imaging area; and a bed provided with a table on which the patient is laid down and a table-supporting unit for supporting said table movably in a longitudinal direction of said table;

said X-ray diagnosis apparatus and said spirally scanning X-ray CT apparatus being located along a path of movement of said table so that said first and second imaging areas are located at positions spaced apart from each other by a predetermined distance;

said X-ray examination apparatus further comprising:
- a memory for storing a distance defined between an imaging center of said first imaging area and a position where a spiral scanning of the patient is commenced in said second imaging area;
- a detector for detecting an amount of movement of said table; and
- table control means for comparing said movement amount of said table with said distance defined between an imaging center of said first imaging area and a position where a spiral scanning is commenced in said second imaging area, to automatically move said table from the imaging center of said first imaging area to said position where a spiral scanning is commenced and vice versa and to automatically perform the stopping of said table.

17. An X-ray examination apparatus comprising:

an X-ray diagnosis apparatus including an X-ray tube and an image intensifier apparatus which face each other through a first imaging area in which a patient is positioned;

a spirally scanning X-ray CT apparatus for producing a sectional image of the patient positioned in a second imaging area; and a bed provided with a table on which the patient is laid down and a table-supporting unit for supporting said table movably in a longitudinal direction of said table;

said X-ray diagnosis apparatus and said spirally scanning X-ray CT apparatus being located along a path of movement of said table so that said first and second imaging areas are located at positions spaced apart from each other by a predetermined distance;

said X-ray examination apparatus further comprising:
- a memory for storing a distance defined between a position where a spiral scanning of the patient is finished in said second imaging area and an imaging center of said first imaging area; and
- a detector for detecting an amount of movement of said table; and
- table control means for comparing said movement amount of said table with said distance defined between a position where a spiral scanning of the patient is finished in said second imaging area and said imaging center of said first imaging area, to automatically move said table from the position where said spiral scanning is finished to said imaging center of said first imaging area and to automatically perform the stopping of said table.

* * * * *